United States Patent
McKay

(10) Patent No.: US 8,713,987 B2
(45) Date of Patent: May 6, 2014

(54) ON-BOARD WATER SPRAY SYSTEM FOR AIRCRAFT

(75) Inventor: Gary E. McKay, Wichita, KS (US)

(73) Assignee: Textron Innovations Inc., Providence, RI (US)

(*) Notice: Subject to any disclaimer, the term of this patent is extended or adjusted under 35 U.S.C. 154(b) by 894 days.

(21) Appl. No.: 12/760,939

(22) Filed: Apr. 15, 2010

(65) Prior Publication Data

US 2011/0252863 A1 Oct. 20, 2011

(51) Int. Cl.
*B64D 47/00* (2006.01)
*B64D 43/00* (2006.01)
*G01M 17/06* (2006.01)
*G01N 19/02* (2006.01)
*B60T 8/56* (2006.01)
*B60T 17/22* (2006.01)
*B64F 5/00* (2006.01)
*G01L 5/28* (2006.01)

(52) U.S. Cl.
CPC ............. *B60T 8/56* (2013.01); *B60T 17/221* (2013.01); *B64F 5/0045* (2013.01); *B60T 2210/12* (2013.01); *B60T 2210/13* (2013.01)
USPC ............ 73/10; 73/118.01; 73/129; 73/146; 239/171; 244/1 R; 244/136

(58) Field of Classification Search
CPC ........ B60T 8/56; B60T 17/221; B64T 5/0045
USPC ............ 73/9–10, 118.01, 121, 128–129, 146; 239/71, 97, 171; 244/1 R, 136
See application file for complete search history.

(56) References Cited

U.S. PATENT DOCUMENTS

| | | | | |
|---|---|---|---|---|
| 2,466,150 A | * | 4/1949 | Burt | 244/114 R |
| 2,664,256 A | * | 12/1953 | Winterringer | 239/171 X |
| 3,645,313 A | * | 2/1972 | Roberts et al. | 152/209.17 |
| 4,313,726 A | * | 2/1982 | Chase | 434/42 |
| 5,918,951 A | | 7/1999 | Rudd, III | |
| 6,175,370 B1 | | 1/2001 | Kunimatsu | |
| 6,684,147 B2 | | 1/2004 | Park et al. | |
| 7,035,725 B1 | | 4/2006 | Park et al. | |
| 7,735,186 B1 | * | 6/2010 | Vogel | 15/320 |
| 8,332,114 B2 | * | 12/2012 | Whittingham | 701/70 |
| 8,412,434 B2 | * | 4/2013 | Rado | 244/1 R X |
| 2001/0019090 A1 | * | 9/2001 | Horev | 244/136 |
| 2002/0014259 A1 | * | 2/2002 | Hahnl | 134/26 |
| 2007/0158449 A1 | * | 7/2007 | Hoffmann et al. | 239/171 X |
| 2008/0154471 A1 | * | 6/2008 | Garcia et al. | B60T 2210/12 |
| 2010/0070115 A1 | * | 3/2010 | Villaume | 701/18 |
| 2013/0126677 A1 | * | 5/2013 | Mark et al. | 244/136 |

FOREIGN PATENT DOCUMENTS

| | | | | | |
|---|---|---|---|---|---|
| DE | 2701695 C | * | 4/1985 | ............ | A01M 17/00 |
| GB | 2462528 A | * | 2/2010 | ............. | G01N 19/02 |

* cited by examiner

*Primary Examiner* — Thomas P Noland
(74) *Attorney, Agent, or Firm* — Lathrop & Gage LLP

(57) ABSTRACT

A system for simulating wet runway conditions by using a liquid container that is placed inside an aircraft. The liquid container is connected to a nozzle that sprays water in front of the wheels of the aircraft. A valve is used to control the flow of water from the nozzle. Systems, such as the braking system of the aircraft, can then be tested in wet runway conditions simulated by the system. The amount of water sprayed from the nozzle can also be electronically controlled in relation to the speed of the aircraft, such that the nozzle sprays a nearly uniform layer of liquid in front of the wheels. The system can also be modified to include two tanks to manipulate the center of gravity of the aircraft.

3 Claims, 4 Drawing Sheets

ON-BOARD WATER SPRAY SYSTEM FOR AIRCRAFT

BACKGROUND OF THE INVENTION

1. Field of the Invention

The invention relates generally to the field of simulating wet surfaces for testing. More specifically, the invention relates to the field of testing the performance of aircraft tires and/or braking systems on wet runways.

2. Description of the Related Art

Conventionally, aircraft braking systems are subject to tests to see how they will perform on wet runways by manually dousing the runway surfaces with water and then landing the plane.

Testing systems have been developed to simulate these conditions. For example, in one system water is distributed onto the runway using a gravity fed tank on a trailer that is being pulled by a motor vehicle. Water is then dropped onto the ground in front of a test wheel which is also located on the trailer.

SUMMARY

Embodiments of the present invention include a system for simulating wet runway conditions. The system, in one embodiment, includes a liquid container situated on an aircraft. A liquid conduit fluidly connects the liquid container to a nozzle that is positioned to spray a liquid onto the ground in front of a wheel of the aircraft. In some embodiments a fan-shaped nozzle is used to produce a spray which creates a substantially uniform application of the liquid on the ground surface. In some embodiments, the fan-shaped spray pattern creates a depth of application that is around 0.04 inches of water.

The container can be a tank system which receives air under pressure from an air source, e.g., bleed air, to compel the delivery of water from the tank to the nozzle. The tank can include a relief valve to avoid overpressurization.

In embodiments, the system can include a liquid flow control system. This system controls the flow of water to the nozzle. It comprises a flow control valve for conditionally metering the amount of flow in the liquid conduit to establish a desirable flow rate of the liquid to the nozzle. This enables the flow control needed, but in yet other embodiments the system can include a controller, e.g., microcomputer. In one respect, the controller can receive on off signals from a switch in the cockpit to turn the spray system on and off.

Once on, some embodiments of the system include a speed sensor and a flow rate meter. The controller receives signals from the speed sensor and flow meter. This enables the system to establish a flow rate that establishes a substantially consistent application depth on the runway that accommodates speed changes. The flow control valve meters using the speed and flow data received to establish a flow rate that is appropriate at the given speed.

In another embodiment, an aircraft system comprises two tanks. A first liquid tank is located on a first side of an initial center of gravity of the aircraft, e.g., in front of the aircraft. The second liquid tank is located on an opposite side of the initial center of gravity for the aircraft, e.g., in back. The center of gravity can be adjusted in flight using a fluid control system that allows for changes in the tank fill levels to effect the change in center of gravity for the aircraft. This dual-tank embodiment can be used in cooperation with a spray system like that discussed above. To do so, one or both of the dual tanks would be fluidly connected to at least one nozzle used to spray a liquid onto a ground surface in front of a wheel of the aircraft to create a simulation of a wet runway.

Also disclosed is an embodiment that is a method for testing aircraft performance. This method involves putting a liquid container on an aircraft; filling the container with a liquid; using air pressure to compel the liquid; regulating flow of the liquid using a flow controlling valve; and applying the flow of liquid to a ground surface in front of a wheel of the aircraft in a substantially uniform manner when the aircraft is moving on the ground surface. This method, in embodiments enables automatically controlling a speed of the flow of the liquid using ground speed and flow rate data and then increasing the openness of the flow control valve if the flow rate value is below an acceptable deviation from an ideal flow rate at the speed; and decreasing the openness of the flow controlling valve if the flow rate value is above an acceptable deviation from the ideal flow rate at the speed. In some embodiments, the automatic control processes are executed in a loop so that the openness of the flow control valve is continually maintained inside acceptable ranges in consideration of ground speed.

BRIEF DESCRIPTION OF THE SEVERAL VIEWS OF THE DRAWINGS

Illustrative embodiments of the present invention are described in detail below with reference to the attached drawing figures, which are incorporated by reference herein and wherein.

DETAILED DESCRIPTION

Figure 1:
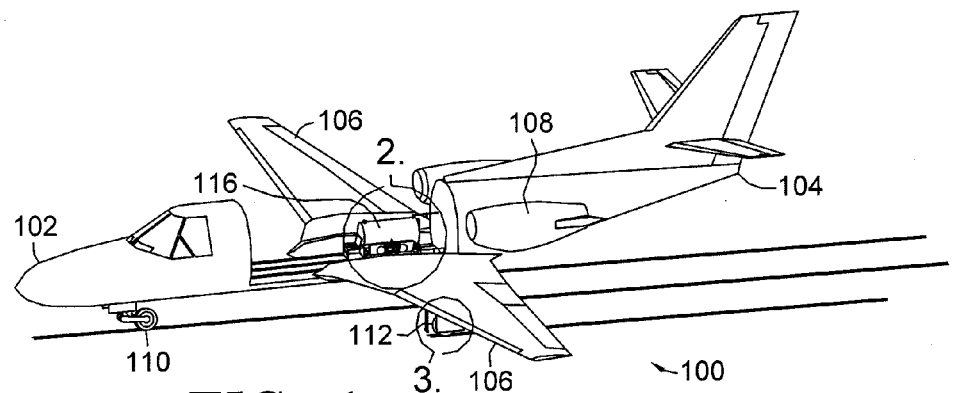
FIG. 1 is a perspective view of an aircraft including the on-board spray systems in one embodiment.

Embodiments of the present invention provide, in part, a system for simulating wet runway conditions. Wet conditions on runways are traditionally simulated using ground vehicles that apply water onto the runway. The present invention provides an independent method to simulate wet runways by using a system that does not require ground vehicles, but can utilize an aircraft 100. FIG. 1 shows the aircraft 100. As is typical, the aircraft has a nose 102, a cockpit 103, tail 104, wings 106, engines 108, a nose wheel 110, and rear wheels/tires 112.

Figure 2:
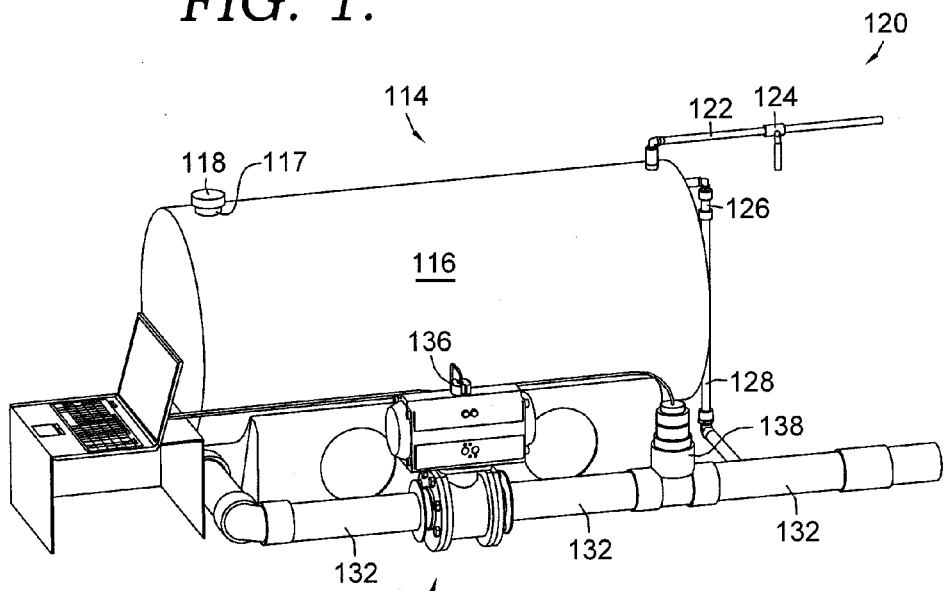
FIG. 2 is a detailed view 2 taken from FIG. 1 showing the liquid supply and flow control components in embodiments.

FIG. 2 shows an on-board water spray system 114 which may be included on the aircraft 100 for testing. The system contains a liquid tank 116. This liquid tank 116 is situated in the aircraft 100. The liquid tank 116 is filled with a liquid, e.g., water, through an opening 117. The opening 117 is closed with a cap 118. The cap 118 is removed when water is being filled into the tank. After the liquid tank 116 is filled up to the desired level, the cap 118 is placed back on the opening 117 to close the opening. The cap 118, when reattached, ensures that no water spills out of the tank when the tank is filled with water. The tank 116 is normally not fully filled with water to ensure that the bleed air can enter into the tank and pressurize the water in the tank effectively, as will be discussed later. The cap 118 is generally placed in position to close the opening 117 even when the system 114 is not in operation, to ensure that unintended objects do not get into the liquid tank 116.

The on-board water spray system may include a tank pressurization system 120. The tank pressurization system 120 is used to control the pressure at which the water inside the tank is stored. The liquid tank 116 is connected to one end of a conduit 122. The other end of conduit 122 is connected to a pressure source which is used to keep the pressure in the liquid tank 116 at a desired level. In one embodiment, bleed air, which is compressed air taken from the engine 108, may be utilized as the source that provides the pressurized air to the liquid tank 116. Alternatively, the water could be mechanically driven by, e.g., a pump system (not shown). An air pressurized tank, however, has been used here in order to avoid limitations existing with mechanical solutions, e.g., lack of flow rate generation capabilities.

The conduit 122 may contain a manual shutoff valve 124, which is used to manually open the tank up to pressurization for testing, or to close off the flow of pressurized air into the liquid tank 116 when the tank does not need to be pressurized, e.g., before or after testing.

As is known by those skilled in the art, regulated bleed air sources are available in most turbine powered aircraft which can be tapped into to supply the required bleed air to conduit 122. Normally the air is available/regulated to approximately 20 psi. This value may, of course, vary considerably depending on the sort of aircraft involved. But generally speaking, most turbine aircraft have some available bleed air arrangement that can be used to pressurize a water tank. In the preferred embodiment, a 20 psi pressure is used. It is likely, however, that the air pressure used will be ramped down from this level to accommodate different system configurations.

The tank 116, in the FIG. 2 embodiment, includes a relief valve 126 and a drain line 128. Relief valve 126 is selected such that it prevents overpressurization in the tank. As discussed above, the pressurized air is at about 20 psi. Thus, tank 116 is adapted to accommodate this elevated pressure. But in case the pressure in the tank somehow reaches unacceptable levels, the relief valve will open up as a precaution. Some excess water may also drain out of the drain line 128 along with the bleed air. Thus, drain line 128 directs the water outside the aircraft.

Figure 3:
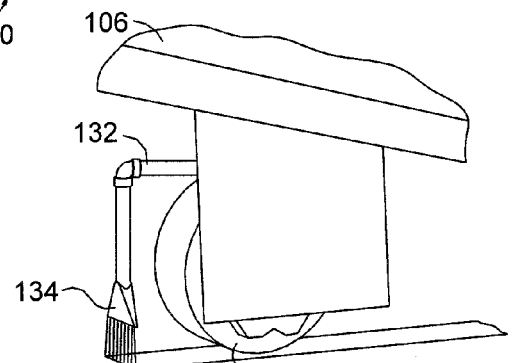
FIG. 3 is detail 3 taken from FIG. 1 showing the nozzle assembly in one embodiment.

The on-board water spray system 114 includes a flow control system 130. Flow control system 130 includes a flow conduit 132. Flow conduit 132 is connected to the liquid tank 116 at a first end, and to a nozzle 134 at a second end. As shown in FIG. 3, the nozzle 134 is placed in front of each of the rear wheels 112 of the aircraft 100. Looking at FIG. 2, it can be seen that only one conduit 132 is shown. But in the preferred embodiment, a substantially symmetrical arrangement on the opposite side of the aircraft would be used to supply identical water spray to the rear wheel on the other side of the aircraft. This could be done using a Y-branching junction to break the water supply in two and supply the nozzle on the opposite side of the aircraft. It should also be noted that for aircraft having two rear wheels on each side, a total of four nozzles and supporting conduit arrangements would be needed.

Similarly, it is contemplated that an additional spray nozzle can similarly be placed in front of the nose wheel 110 of the aircraft to test for steering authority. This forward nozzle could be supplied from a conduit branched from the already-depicted tank, or alternatively from a separate tank arrangement. Thus, although the embodiment shown in FIGS. 1-4 depict only one nozzle, it will be desirable in many instances to use dual nozzles that spray in front of both rear wheels.

It should be noted that, in yet another embodiment, dual tanks (one forward, and one aft) could be used to create a center-of-gravity (CG) manipulation system. Oftentimes, it is desirable in aircraft testing to observe aircraft performance under a range of CG locations to define a safe CG range. In order to accomplish this, the front and rear tanks could be selectively filled to different relative values to thus, change CG in flight. Starting with partially filled front and back tanks, and then using an intertank pumping capability to transfer water from the front tank to the back, or vice versa to accomplish a CG shift.

The nozzle 134 sprays the liquid almost directly in front of the rear wheel. In one embodiment, nozzle 134 releases the liquid in a fan shaped spray pattern. The fan shaped spray pattern out of nozzle 134 ensures that the liquid is sprayed in front of the wheels with substantial uniformity. In the preferred embodiment, the layer of water created is about 0.04 inches deep, which is generally accepted as being representative of wet runway conditions.

As shown in FIG. 2, the on-board water spray system may include a flow control system 130 that is designed to manage the quantity of water that is sprayed out of the nozzle 134. The flow of water being sprayed out of the nozzle is controlled by a control valve 136. The control valve 136 may be a servo-controlled valve, or some other known equivalent. This control valve 136 can be opened, closed, or put in intermediate positions to establish a desirable rate of flow of the water from the tank 116 to the nozzle 134. The flow control system includes a flow meter 138. The flow meter 138 quantifies the amount of liquid that is flowing out of the nozzle 134 at a given time.

Figure 4:
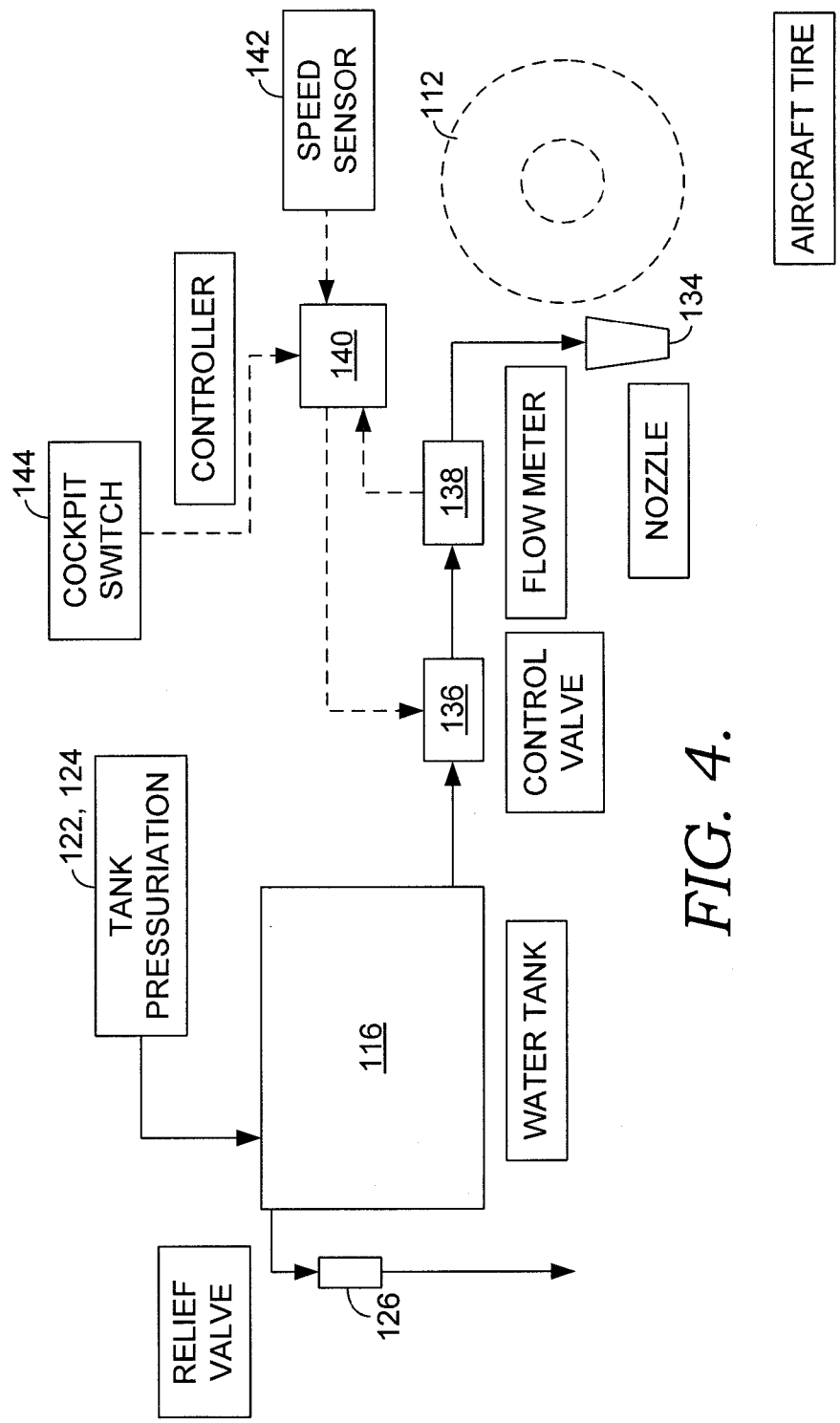
FIG. 4 is a schematic showing the interelation of the many components in embodiments.

As shown in FIG. 4, the flow control system 130 includes a controller 140. Controller 140 could be one of numerous known smart devices, e.g., a personal computer, a programmable logic controller, microcomputing device, or a single board device. The controller 140 is electrically connected to the control valve 136, the flow meter 138, and a speed sensor 142 in a known manner. The speed sensor 142 may consist of a global positioning system; or derive readings from an electro-mechanical wheel speed detector arrangement commonly used with anti-skid systems. Regardless of particular configuration, the speed sensor 142 measures the ground speed of the aircraft 100.

The controller 140 is also connected to a cockpit switch 144. The cockpit switch 144 is situated in the cockpit 103. The cockpit switch 144 enables a user to start and stop the flow control system 130 from the cockpit of the aircraft 100 while maneuvering the aircraft 100 by sending a signal to the controller using known technologies.

Figure 5:
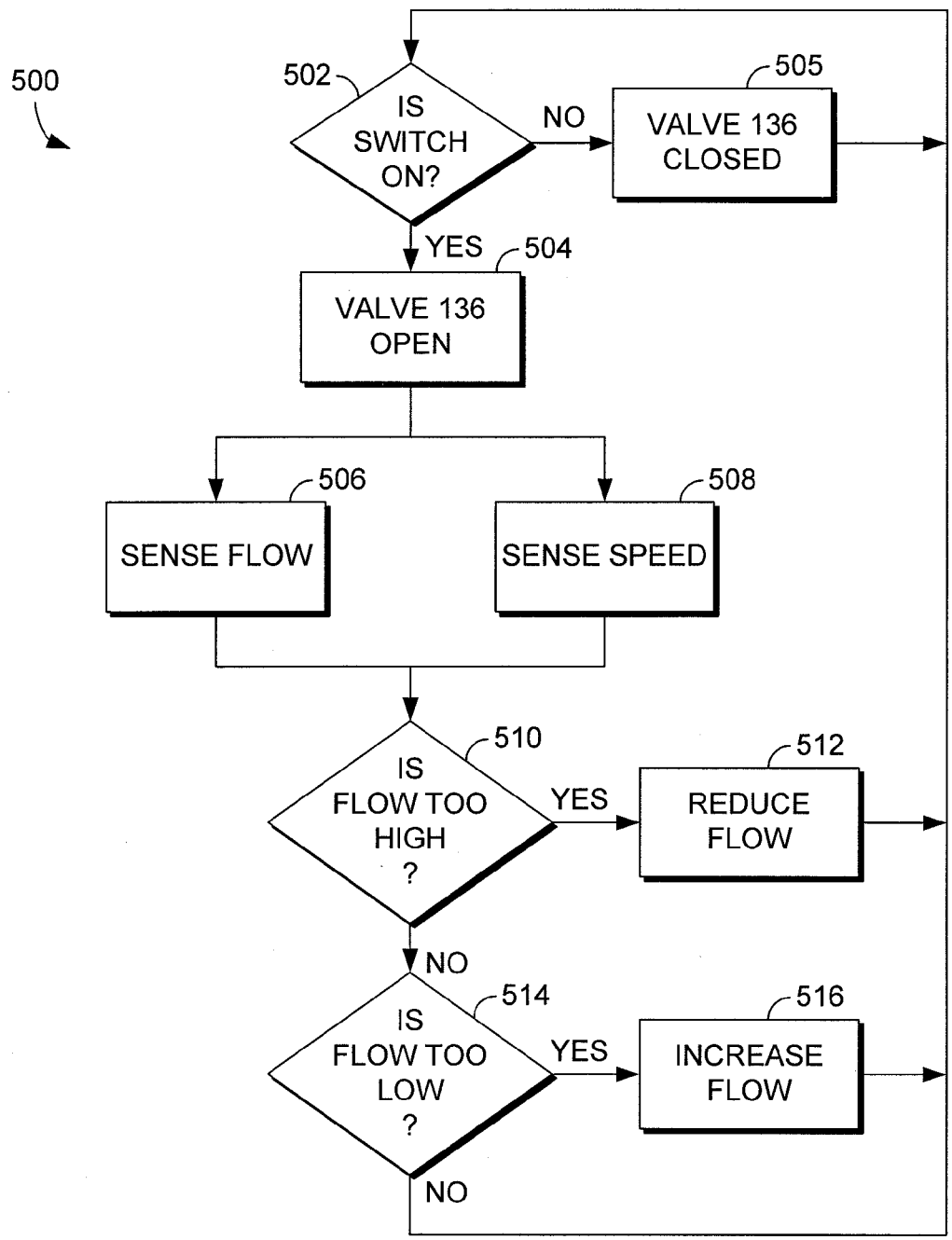
FIG. 5 is a flow diagram showing the processes running on the system controller in embodiments.

FIG. 5 is a flow chart including steps that outline the processes running on controller 140. In a first step 502, an inquiry is made as to whether the switch 144 in the cockpit is on. So long as switch 144 is off, the flow control valve 136 will remain closed in a step 505 and the process will loop between steps 505 and 502 indefinitely until the system is switched on. Once switch 144 is flipped to on, the controller (in step 502) recognizes this and valve 136 is opened up in a step 504. Initially, in step 504, the valve 136 will be opened to a starting point that is estimated to provide a starting flow rate. The controller then receives this flow rate from flow meter 138 and also the sensed speed from speed sensor 142 in steps 506 and 508, respectively.

Once this information has been received by the controller 140, the process moves on to a query step 510 in which a determination is made as to whether the flow rate is too high considering the speed sensed from the speed sensor 142. The controller 140 compares the inputs from the flow meter 138 and the speed sensor 142 with a pre-set look up table.

Figure 6:
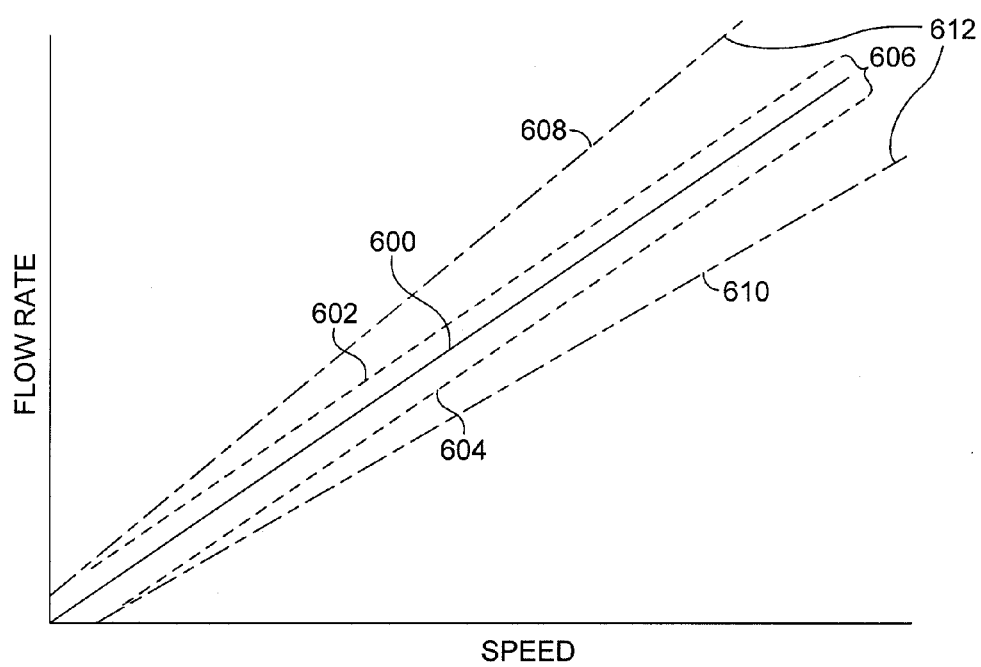
FIG. 6 is a chart which reflects how the deadband ranges are created for the lookup tables used in an embodiment of the invention.

Referring to FIG. 6, a graphical representation of the data included in the look up table can be seen. Referring to the figure, a line 600 is a linear plot of the ideal flow rates at each speed sensed for the aircraft to maintain the water deposited on the runway at a desired depth, e.g., 0.04 inches in one embodiment. In one embodiment, a constant dead band range 606, e.g., plus or minus 0.5 gpm in some embodiments, is created about ideal line 600 between maximum 602 and minimum 604. Lines 602 and 604, in this embodiment, are parallel with, and equidistant from ideal line 600. The displacement of each of lines 602 and 604 from line 600 represents a predetermined acceptable deviation from the ideal. If the sensed flow rate value at the sensed speed exceeds the upper boundary line 602, then the answer to query step 510 will be yes, and the flow will be reduced in a step 512. More specifically, the controller 140 sends a signal to the flow control valve 136 causing it to close slightly. Once the flow control valve has thus been closed to an extent in step 512, the process loops back up and is reintroduced to step 502.

If the sensed flow rate at the given speed falls below upper boundary line 602, then the process moves on to a query step 514 where a determination is made as to whether the flow rate is too low. In this step, if the sensed flow rate at the sensed speed falls below the values at predetermined lower boundary line 604, then the answer in step 514 will be yes, and the process will move on to a step 516 in which the controller will send a signal to flow control valve 136 opening it up slightly, and the process will then loop back up to step 502.

If, however, in step 514 the flow rate value at the sensed speed is above line 604, then the process immediately loops back up and is reintroduced to step 502 without executing step 516.

It can be seen that the continuous looping process in flow 500 will result in the continuous incremental adjustment in the openness of flow control valve 136 when the system is active.

In an alternative embodiment, a maximum line 608 and a minimum line 610 together create an increasingly expanding range 612 about ideal line 600. This embodiment will result in the acceptable deviation for flow rate being greater at higher ground speeds detected.

In terms of the signaling, the output of the controller 140 being received by the control valve 136 may be a DC voltage signal ranging from zero to 10 volts. An output of zero volts from the controller may close the control valve 136 completely, an output of 10 volts may open the control valve 136 fully, and the intermediate values may open the control valve 136 to varying degrees to establish the desired amount of flow from the nozzle 134. In this case, the flow reductions made in step 512 will be made incrementally with each loop, as will the flow increases of step 516 with each execution.

These FIG. 5 processes of the controller acting in cooperation with the speed sensor 142, flow meter 138, and flow control valve 136 enable the current flow of water from the nozzle 134 to be regulated so that a nearly uniform layer of water is deposited onto the ground in front of the wheel 112. A depth of 0.04 inches of water is considered to be generally representative of wet runway conditions. Thus, in a preferred embodiment, the dead band ranges (e.g., ranges 606 and 612) are selected such that they result in a consistent, nearly uniform, layer of water that is 0.04 inches deep regardless of the current, and/or changing ground speeds of the aircraft. Thus, when the ground speed of the aircraft 100 increases, the controller 140 opens valve 136 to further increase the flow of water out of the nozzle 134. When the speed of the aircraft decreases, the controller 140 closes valve 136 further. In this manner varying speeds are accommodated.

When the pilot (or another) moves switch 144 to "off" position, this will be recognized in looping step 502, and the valve 136 is closed in a step 505. The process will remain in a mode looping between steps 502 and 505 until the switch is flipped back on.

Systems of the aircraft 100 can now be tested in wet runway conditions. For example, the performance of the braking system of an aircraft 100 may be evaluated in the simulated wet runway conditions. Similarly, the performance of the tires of the aircraft 100 may be tested in these simulated wet runway conditions.

After a testing run has been completed, the tank is able to be refilled. The switch will be off, and flow control valve 136, thus, will be closed. Additionally, the user will close off the tank from the bleed air using valve 124. Then, the user can remove the pressure releasing safety cap 118, and fill the tank 116 with water.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and sub combinations are of utility and may be employed without reference to other features and sub combinations and are contemplated within the scope of the claims. Not all steps listed in the various figures need be carried out in the specific order described.

The invention claimed is:

1. A system for simulating wet runway conditions, the system comprising:
 a tank situated on an aircraft which receives air under pressure from an air source to compel the delivery of water from the tank to a nozzle;
 a liquid conduit fluidly connecting the tank to the nozzle; and the nozzle positioned to spray water onto a ground surface in front of a wheel of the aircraft;
 wherein the tank includes a relief valve which releases air to the atmosphere upon the pressure in the tank reaching a predetermined value to avoid over-pressurization in the tank; and
 wherein the air source is bleed air from an engine on the aircraft.

2. The system of claim 1 wherein the bleed air is delivered from a regulated source of air originating from the compressor section of the engine in an air conduit.

3. The system of claim 2 wherein the air conduit includes a shut off valve.

* * * * *